United States Patent
Dasgupta et al.

(10) Patent No.: US 7,408,055 B2
(45) Date of Patent: Aug. 5, 2008

(54) PROMOTER MOLECULES FOR USE IN PLANTS

(75) Inventors: Santanu Dasgupta, Bangalore (IN); Wei Wu, St. Louis, MO (US); Brendan S. Hinchey, Mystic, CT (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 11/352,157

(22) Filed: Feb. 10, 2006

(65) Prior Publication Data

US 2006/0179516 A1  Aug. 10, 2006

Related U.S. Application Data

(60) Provisional application No. 60/651,675, filed on Feb. 10, 2005.

(51) Int. Cl.
*C12N 15/63* (2006.01)
*C12N 15/82* (2006.01)
*C12N 5/04* (2006.01)

(52) U.S. Cl. .................. 536/24.1; 435/320.1; 435/419; 435/468

(58) Field of Classification Search ........................ None
See application file for complete search history.

(56) References Cited

U.S. PATENT DOCUMENTS

| 5,593,874 A | 1/1997 | Brown et al. ................. 800/279 |
| 5,641,876 A | 6/1997 | McElroy et al. ............. 536/24.1 |
| 5,659,122 A | 8/1997 | Austin ..................... 800/317.3 |
| 6,747,189 B1 | 6/2004 | McElroy et al. ............. 800/287 |

OTHER PUBLICATIONS

Kim et al. 1994, Plant Molecular Biology 24: 105-117.*
Peng et al 1995, Plant Mol. Biol. 27:91-104.*
Kikuchi et al. 2003, Genbank accession: AK066587 or AK104714.*
Wing et al. 2003, Genbank accession: AC140006.*
Database Genbank, Database accession No. AC011915, 2001.
Database Genbank, Database accession No. AC104474, 2002.
Database Genbank, Database accession No. AC140006, 2003.
Database Genbank, Database accession No. AF129511, 2000.
Database Genbank, Database accession No. AK104714, 2003.
Database Genbank, Database accession No. AK106150, 2003.
Database Genbank, Database accession No. AK221042, 2005.
Database Genbank, Database accession No. AY070727, 2001.
Database Genbank, Database accession No. AY093969, 2002.
Database Genbank, Database accession No. AY647949, 2004.
Database Genbank, Database accession No. BX826351, 2004.
Database Genbank, Database accession No. DQ226686, 2006.
Fiebig et al.; "Alterations in CER6, a gene identical to CUT1, differentially affect long-chain lipid content on the surface of pollen and stems," *Plant Cell*, 12:2001-2008, 2000.
Millar et al.; "CUT1, an Arabidopsis gene required for cuticular wax biosynthesis and pollen fertility, encodes a very-long-chain fatty acid condensing enzyme," *Plant Cell*, 11(5):825-838, 1999.

* cited by examiner

*Primary Examiner*—Elizabeth Mcelwain
*Assistant Examiner*—Li Zheng
(74) *Attorney, Agent, or Firm*—Sonnenschein Nath & Rosenthal LLP

(57) ABSTRACT

The present invention provides DNA molecules isolated from *Oryza sativa* plants and useful for expressing transgenes in plants. The present invention also provides expression constructs containing the DNA molecules useful for expressing transgenes in plants. The present invention also provides transgenic plants and seeds containing the DNA molecules useful for expressing transgenes in plants.

20 Claims, 1 Drawing Sheet

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial sequence
<220> FEATURE:
<223> OTHER INFORMATION: Synthetic construct

<400> SEQUENCE: 1
cactctcgta gctagtacg                                                  19

<210> SEQ ID NO 2
<211> LENGTH: 24
<212> TYPE: DNA
<213> ORGANISM: Artificial sequence
<220> FEATURE:
<223> OTHER INFORMATION: Synthetic construct

<400> SEQUENCE: 2
actccctcct ccgttctata aaaa                                            24
```

<210> SEQ ID NO 3
<211> LENGTH: 1827
<212> TYPE: DNA
<213> ORGANISM: Oryza sativa

<400> SEQUENCE: 3

```
tccctcctcc gttctataaa aaaccaacct actatcggat gtgacacatc ctaatactat        60
gaatctggat atacatcata ctaaaatatg ttatatccgg ttctagattc gttttatgg       120
aacggaggga gtattctgtc atcagctatc actgctctgc ctgaacttgt ctgagctatt       180
actactgtag tatatgaatt tatgaagtgg agtctcgtaa caaaaatacg agtatactcc       240
gtactgtact acccttatca ggattcaagg atactaggag tatagcatta ccagatcagg       300
cacttagatg tggccatcca agagtaatg gtaatagcct aataggagta ccatctacta       360
ttgatctttc aaaaaaaaa gtactagtat agaagtagta tccagctaga gctgcttaac       420
agggtcagaa tttgtccaaa cagagcttgt aatgcacact gacgaagtcg atccgatcga       480
atcagagtca acatttaaag agtactattt cgaagtaaaa ctgttcagtt cttacaagat       540
tacatgtgaa tttgcaagac ttggacatga gtgttcatct cgtagtttaa tgatgggtac       600
ccaacctgca acaacagtgc tttaaattgt acaagcagag ggtaccaaca gagtaatttg       660
cacatgcagt cctgaacctg atgccattgc gaaacacaca accctatacg gtgcagatgc       720
aagggagccc aattcagtcc cagccattat ctgtattgcc gtacttccgc agggaaagtt       780
accctctcat ctgatctacc attgcataca tctcaaaagg aagtgagtaa aaagaaaaac       840
aggaccaatc ttcagagata agtttttgaa acctatcttc agagataagt tcactcggcg       900
ataggagagg acctgatttg gactcaaatc aggtgttgac gaatagagta gcaagagttt       960
tttcgacggg tcaagacctc aagggtctta acagttgaac taactcggtt atgatttgga      1020
cacttggtga ttaactactg ataatagtac tacttattgt tattggcttg ttacatcatt      1080
cggtgctcaa aaatcagatg caaatttaga tgggacagac agcagctact agcaacataa      1140
gagaattatg ttcagtgtat catgcatgac taaactctga acgtactcac ctggatccag      1200
atgcgagcag tacagtacct gtgcacattg cttgtgtatt actccactta attacgaact      1260
ctattatttt cctccgataa tgcccgcaga acaaggttgt cactgaaaaa tggtcctctc      1320
cagagtccag gagctatagg aggagtatga tactccttag caatcatata ctcatatgac      1380
atatccaaat tgacaccggg gttaagccgt taaccgtcac tacgagttgc acttgtataa      1440
acaaaaaaca agggagaaaa ccttgtgtcc cccccatgat gcagaaatct aataagagca      1500
gcccaacgct tccggttggt ggcggtagac cggcctcttt aaactacccc atccgcccca      1560
gatttatcaa ttactcctcg tcatctcgtc tcgtctccgc caccgtgcgc gcgtcccta       1620
tattagaccc cccaaccggg caccggacac accatcacca acacaccact gcaaacccat      1680
ccgcctccgc accgcatcgc acctacaaat tgtgcacgct gcaccgctca aaaaaagaa       1740
gaaactaaag tcgtacgtag gacgcggcgt gcgagcgttg gtgcggtgcg cggcggcgcg      1800
cggggaagta gtgagagcat cgatcat                                          1827
```

<210> SEQ ID NO 4
<211> LENGTH: 26
<212> TYPE: DNA
<213> ORGANISM: Artificial sequence
<220> FEATURE:
<223> OTHER INFORMATION: Synthetic construct

<400> SEQUENCE: 4

-continued

```
cactagagat cttccctcct ccgttc                                          26
```

<210> SEQ ID NO 5
<211> LENGTH: 24
<212> TYPE: DNA
<213> ORGANISM: Artificial sequence
<220> FEATURE:
<223> OTHER INFORMATION: Synthetic construct

<400> SEQUENCE: 5

```
ggaatcgcga tgaatgatcg atgc                                            24
```

<210> SEQ ID NO 6
<211> LENGTH: 1696
<212> TYPE: DNA
<213> ORGANISM: Oryza sativa

<400> SEQUENCE: 6

```
tattctgtca tcagctatca ctgctctgcc tgaacttgtc tgagctatta ctactgtagt     60
atatgaattt atgaagtgga gtctcgtaac aaaaatacga gtatactccg tactgtacta   120
cccttatcag gattcaagga tactaggagt atagcattac cagatcaggc acttagatgt   180
ggccatccaa agagtaatgg taatagccta ataggagtac catctactat tgatctttca   240
aaaaaaaaag tactagtata gaagtagtat ccagctagag ctgcttaaca gggtcagaat   300
ttgtccaaac agagcttgta atgcacactg acgaagtcga tccgatcgaa tcagagtcaa   360
catttaaaga gtactatttc gaagtaaaac tgttcagttc ttacaagatt acatgtgaat   420
ttgcaagact tggacatgag tgttcatctc gtagtttaat gatgggtacc caacctgcaa   480
caacagtgct ttaaattgta caagcagagg gtaccaacag agtaatttgc acatgcagtc   540
ctgaacctga tgccattgcg aaacacacaa ccctatacgg tgcagatgca agggagccca   600
attcagtccc agccattatc tgtattgccg tacttccgca gggaaagtta ccctctcatc   660
tgatctacca ttgcatacat ctcaaaagga agtgagtaaa aagaaaaca ggaccaatct   720
tcagagataa gttttttgaaa cctatcttca gagataagtt cactcggcga taggagagga   780
cctgatttgg actcaaatca ggtgttgacg aatagagtag caagagtttt ttcgacgggt   840
caagacctca agggtcttaa cagttgaact aactcggtta tgatttggac acttggtgat   900
taactactga taatagtact acttattgtt attggcttgt tacatcattc ggtgctcaaa   960
aatcagatgc aaatttagat gggacagaca gcagctacta gcaacataag agaattatgt  1020
tcagtgtatc atgcatgact aaactctgaa cgtactcacc tggatccaga tgcgagcagt  1080
acagtacctg tgcacattgc ttgtgtatta ctccacttaa ttacgaactc tattattttc  1140
ctccgataat gcccgcagaa caaggttgtc actgaaaaat ggtcctctcc agagtccagg  1200
agctatagga ggagtatgat actccttagc aatcatatac tcatatgaca tatccaaatt  1260
gacaccgggg ttaagccgtt aaccgtcact acgagttgca cttgtataaa caaaaaacaa  1320
gggagaaaac cttgtgtccc ccccatgatg cagaaatcta ataagagcag cccaacgctt  1380
ccggttggtg gcgtagacc ggcctctttta aactacccca tccgcccag atttatcaat   1440
tactcctcgt catctcgtct cgtctccgcc accgtgcgcg cgtccctat attagacccc    1500
ccaaccgggc accggacaca ccatcaccaa cacaccactg caaacccatc cgcctccgca  1560
```

```
ccgcatcgca cctacaaatt gtgcacgctg caccgctcaa aaaaaagaag aaactaaagt    1620
cgtacgtagg acgcggcgtg cgagcgttgg tgcggtgcgc ggcggcgcgc ggggaagtag    1680
tgagagcatc gatcat                                                    1696
```

US 7,408,055 B2

PROMOTER MOLECULES FOR USE IN PLANTS

PRIORITY CLAIM AND INCORPORATION OF THE SEQUENCE LISTING

This application claims benefit of priority to the following application: U.S. Provisional Application Ser. No. 60/651,675, entitled "Promoter Molecules for Use in Plant" and filed 10 Feb. 2005. Two copies of the sequence listing (Seq. Listing Copy 1 and Seq. Listing Copy 2) and a computer readable form of the sequence listing, all on CD-ROMS, each containing the file named "Cut-1.ST25-1.txtB", which is 6,144 bytes (measured in MS-DOS) and was created on Feb. 9, 2006, are hereby incorporated by reference.

FIELD OF THE INVENTION

The invention relates to the field of plant molecular biology and plant genetic engineering and DNA molecules useful for the expression of transgenes in plants.

BACKGROUND

While previous work has provided a number of regulatory elements useful to affect gene expression in transgenic plants, there is still a great need for novel regulatory elements with beneficial expression characteristics. In particular, there is a need for regulatory elements that are capable of directing expression of transgenes in transgenic crop plants at high levels and in particular tissues, organs, or during specific developmental stages of plant growth.

Useful regulatory elements can be isolated from genes having a desired pattern and/or level of expression of the gene. For present invention inventors looked at the plant cuticle genes due to the function of plant cuticle gene in the nature. All plant cuticles contain waxes, i.e. highly lipophilic compounds that lie both within the cuticular matrix and on its surface as an amorphous film. These films render the plant surfaces hydrophobic. They prevent the formation of stable, macroscopic water phases and, hence, the germination of many plant pathogens. Regulatory elements from genes involved in wax production can provide unique expression pattern that can be utilized for modifying plant phenotypes by expressing transgene controlled by such elements.

One such gene involved in wax production is CUT1 which was described by Millar et al., Plant Cell, 5:825-838 (1999) and Fiebig et al., Plant Cell, 12:2001-2008 (2000). A rice CUT1 gene was used for isolating regulatory elements of the present invention to obtain a desired expression pattern of a transgene as presented here in.

SUMMARY OF THE INVENTION

This invention provides promoters isolated from the regulatory region of a rice CUT1 gene having the nucleotide sequence of SEQ ID NO: 3, more preferably SEQ ID NO:6 which are useful for expressing transgenes in plants. More specific aspects of the invention are isolated DNA molecule having promoter function and comprising (a) at least 50 contiguous bases from SEQ ID NO:6; (b) at least 1000 contiguous nucleotides having at least 85% identity to a window of 1000 nucleotides in SEQ ID NO:6; (c) a derivative of a rice CUT1 promoter with SEQ ID NO:6; or (d) a fragment of a rice CUT1 promoter with SEQ ID NO:6.

Another embodiment of the invention provides recombinant DNA constructs comprising any of the promoters of this invention operably linked to DNA to be transcribed. In another embodiment the invention provides a transgenic plant containing the promoter and the seed of the transgenic plant.

DETAILED DESCRIPTION OF THE INVENTION

Figure 1:
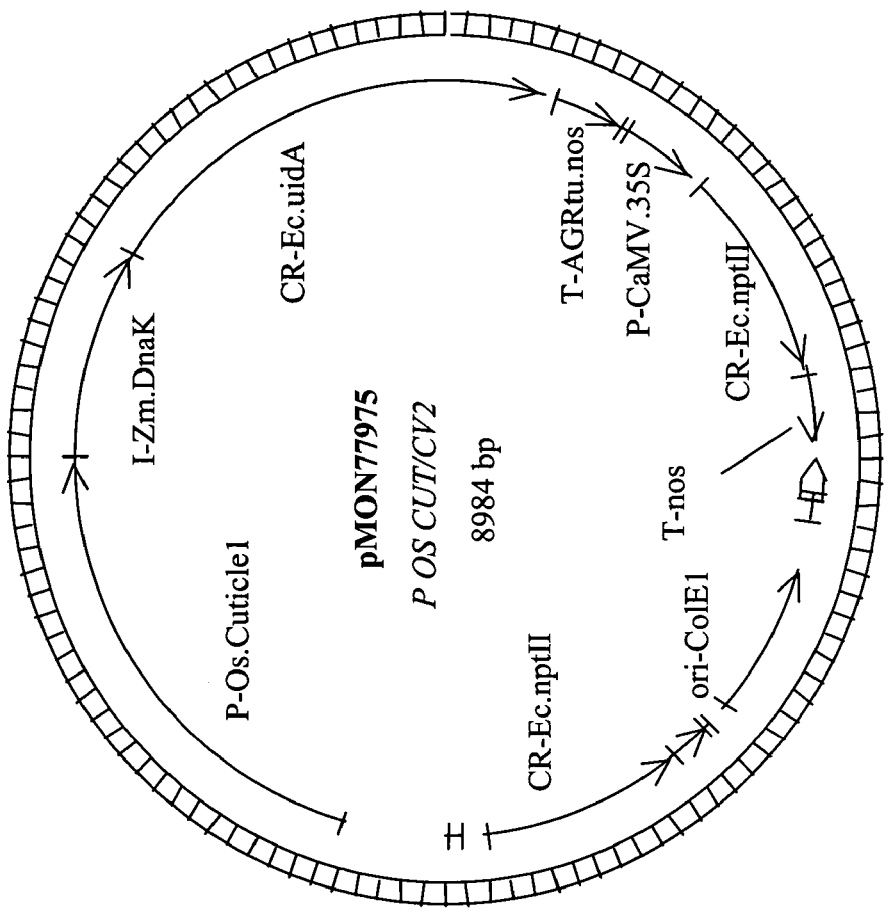
FIG. 1 represents plasmid map of pMON 77975.

As used herein, "promoter" means a region of DNA sequence that is essential for the initiation of transcription of DNA, resulting in the generation of an RNA molecule that is complimentary to the transcribed DNA; this region may also be referred to as a "5' regulatory region." Promoters are located upstream of the coding sequence to be transcribed and have regions that act as binding sites for RNA polymerase and have regions that work with other factors to promote RNA transcription. More specifically, basal promoters in plants comprise canonical regions associated with the initiation of transcription, such as CAAT and TATA boxes. The TATA box element is usually located approximately 20 to 35 nucleotides upstream of the initiation site of transcription. The CAAT box element is usually located approximately 40 to 200 nucleotides upstream of the start site of transcription. The location of these basal promoter elements result in the synthesis of an RNA transcript comprising nucleotides upstream of the translational ATG start site. The region of RNA upstream of the ATG is commonly referred to as a 5' untranslated region or 5' UTR. It is possible to use standard molecular biology techniques to make combinations of basal promoters, that is regions comprising sequences from the CAAT box to the translational start site, with other upstream promoter elements to enhance or otherwise alter promoter activity or specificity.

As used herein "promoter activity" characterizes a DNA sequence which initiates transcription of RNA from adjacent downstream DNA.

Promoters are involved in recognition and binding of RNA polymerase II and other proteins such as transcription factors (trans-acting protein factors that regulate transcription) to initiate transcription of an operably linked gene. Promoters may themselves contain sub-elements such as cis-elements or enhancer domains which effect the transcription of operably linked genes.

The promoters of this invention may be altered to contain "enhancer DNA" to assist in elevating gene expression. As is known in the art certain DNA elements can be used to enhance the transcription of DNA. These enhancers often are found 5' to the start of transcription in a promoter that functions in eukaryotic cells, but can often be inserted upstream (5') or downstream (3') to the coding sequence. In some instances, these 5' enhancer DNA elements are introns. Among the introns that are particularly useful as enhancer DNA are the 5' introns from the rice actin 1 gene (see U.S. Pat. No. 5,641,876), the rice actin 2 gene, the maize alcohol dehydrogenase gene, the maize heat shock protein 70 gene (U.S. Pat. No. 5,593,874), the maize shrunken 1 gene, the light sensitive 1 gene of *Solanum tuberosum*, and the heat shock protein 70 gene of *Petunia hybrida* (U.S. Pat. No. 5,659,122).

As used herein, the term "percent sequence identity" refers to the percentage of identical nucleotides between two segments of a window of optimally aligned DNA. Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction times 100. The comparison of one or more DNA sequences may be to a full-length DNA sequence or a portion thereof, or to a longer DNA sequence.

DNA Isolation and Modification Methods

Any number of methods well known to those skilled in the art can be used to isolate fragments of a DNA molecule disclosed herein. For example, PCR (polymerase chain reaction) technology can be used to amplify flanking regions from a genomic library of a plant using publicly available sequence information. A number of methods are known to those of skill in the art to amplify unknown DNA sequences adjacent to a core region of known sequence. Methods include but are not limited to inverse PCR (IPCR), vectorette PCR, Y-shaped PCR, and genome walking approaches. DNA molecule fragments can also be obtained by other techniques such as by directly synthesizing the fragment by chemical means, as is commonly practiced by using an automated oligonucleotide synthesizer. For the present invention, the DNA molecules were isolated by designing PCR primers based on available sequence information.

Those of skill in the art are familiar with the standard resource materials that describe specific conditions and procedures for the construction, manipulation, and isolation of macromolecules (e.g., DNA molecules, plasmids, etc.), as well as the generation of recombinant organisms and the screening and isolation of DNA molecules.

DNA Constructs

As used herein, the term "DNA construct" means an artificially assembled DNA segment to be transferred into one or more cell or target tissue of a desired organism. Typically, the construct will include the gene of a particular interest, a marker gene and appropriate control sequences.

As used herein, "operably linked" means the association of two or more DNA fragments in a DNA construct so that the function of one, e.g. protein-encoding DNA, is affected by the other, e.g. a promoter. For example, a promoter is operably linked to a gene of interest if the promoter regulates or mediates transcription of the gene of interest in a cell.

For the practice of the present invention, conventional compositions and methods for preparing and using constructs and host cells are well known to one skilled in the art, see for example, J. F. Sambrook, D. W. Russell, and N. Irwin. (2000) *Molecular Cloning: A Laboratory Manual*, 3$^{rd}$ edition Volumes 1, 2, and 3. Cold Spring Harbor Laboratory Press, hereafter referred to as Sambrook et al., 2000.

Constructs of the present invention would typically contain a CUT1 promoter element, with optional enhancer DNA, operably linked to transcribable DNA, e.g. for encoding a protein or a gene suppression RNA, and a polyadenylation site.

Thus, one embodiment of the invention is a polynucleotide molecule such as provided in SEQ ID NO: 3 or SEQ ID NO: 6, operably linked to a transcribable DNA molecule. The transcription of such a DNA molecule will be caused upon introduction of said construct into a plant cell or a plant at a level or in a tissue or developmental stage that is characteristic of SEQ ID NO:3 or SEQ ID NO: 6 as shown in examples of the present disclosure. Such a transcription of operably linked DNA molecules can be altered by adding or deleting other elements in a construct. In some cases, the transcribable DNA molecule comprises a protein-coding region of a gene, and the promoter provides for transcription of a functional mRNA molecule that is translated and expressed as a protein product. Constructs may also be constructed for transcription of antisense RNA molecules or other similar inhibitory RNA molecules in order to suppress expression of a specific gene of interest in a target host cell.

Thus, in one preferred embodiment, a DNA molecule of the present invention as shown in SEQ ID NO: 3 or SEQ ID NO: 6 is incorporated into a construct such that a DNA molecule of the present invention is operably linked to a transcribable DNA molecule that provides for a selectable, screenable, or scorable marker. Markers for use in the practice of the present invention include, but are not limited to transcribable DNA molecules encoding β-glucuronidase (GUS), green fluorescent protein (GFP), luciferase (LUC), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art. Herbicides for which transgenic plant tolerance has been demonstrated and the method of the present invention can be applied, include but are not limited to: glyphosate, glufosinate, sulfonylureas, imidazolinones, bromoxynil, delapon, cyclohezanedione, protoporphyrionogen oxidase inhibitors, and isoxaflutole herbicides. DNA molecules encoding proteins involved in herbicide tolerance are known in the art, and include, but are not limited to a DNA molecule encoding 5-enolpyruvylshikimate-3-phosphate synthase (EPSPS) described in U.S. Pat. Nos. 5,627,061, 5,633,435, 6,040,497 and in 5,094,945 for glyphosate tolerance, all of which are hereby incorporated by reference; a DNA molecule encoding bromoxynil nitrilase (Bxn) described in U.S. Pat. No. 4,810,648 for Bromoxynil tolerance, which is hereby incorporated by reference; a DNA molecule encoding phytoene desaturase (crtI) described in Misawa, et al, (1993) *Plant J.* 4:833-840 and Misawa, et al, (1994) *Plant J.* 6:481-489 for norflurazon tolerance; a DNA molecule encoding acetohydroxyacid synthase (AHAS, aka ALS) described in Sathasivan, et al. (1990) *Nucl. Acids Res.* 18:2188-2193 for tolerance to sulfonylurea herbicides; and the bar gene described in DeBlock, et al. (1987) *EMBO J.* 6:2513-2519 for glufosinate and bialaphos tolerance.

In one embodiment of the invention, a DNA molecule as shown in SEQ ID NO: 3 or SEQ ID NO: 6 is incorporated into a construct such that a DNA molecule of the present invention is operably linked to a transcribable DNA molecule that is a gene of agronomic interest, e.g., a gene that provides a desirable characteristic associated with plant morphology, physiology, growth and development, yield, nutritional enhancement, disease or pest resistance, herbicide resistance or environmental or chemical tolerance. The expression of a gene of agronomic interest is desirable in order to confer an agronomically important trait Alternatively, a transcribable DNA molecule can effect the above mentioned phenotypes by encoding a RNA molecule that causes the targeted suppression of expression of an endogenous gene, for example via antisense, dsRNA, or co-suppression-mediated mechanisms. The RNA could also be a catalytic RNA molecule (i.e., a ribozyme) engineered to cleave a desired endogenous mRNA product. Thus, any DNA molecule that encodes a protein or mRNA that expresses a phenotype or morphology change of interest may be useful for the practice of the present invention.

Constructs of the invention are generally double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *Agrobacterium* cells, permits the integration of the T-DNA into the genome of a plant cell. The constructs also contain the plasmid backbone DNA segments that provide replication function and antibiotic selection in bacterial cells, for example, an *E. coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, or LBA4404, however, other strains known to those skilled in the art of plant transformation can function in the present invention.

Transformed Plants And Plant Cells

As used herein, the term "transformed" refers to a cell, tissue, organ, or organism into which has been introduced a foreign DNA molecule, such as a construct. The introduced DNA molecule may be integrated into the genomic DNA of the recipient cell, tissue, organ, or organism such that the introduced DNA molecule is inherited by subsequent progeny. A "transgenic" or "transformed" cell or organism also includes progeny of the cell or organism and progeny produced from a breeding program employing such a transgenic plant as a parent in a cross and exhibiting an altered phenotype resulting from the presence of a foreign DNA molecule. A plant transformation construct containing a DNA molecule of the present invention may be introduced into plants by any plant transformation method. Methods and materials for transforming plants by introducing a plant expression construct into a plant genome in the practice of this invention can include any of the well-known and demonstrated methods including electroporation as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; *Agrobacterium*-mediated transformation as illustrated in U.S. Pat. Nos. 5,824,877; 5,591,616; 5,981,840; and 6,384,301; and protoplast transformation as illustrated in U.S. Pat. No. 5,508,184, all of which are hereby incorporated by reference.

Methods for specifically transforming dicots are well known to those skilled in the art. Transformation and plant regeneration using these methods have been described for a number of crops including, but not limited to, cotton (*Gossypium hirsutum*), soybean (*Glycine max*), peanut (*Arachis hypogaea*), and members of the genus *Brassica*.

Methods for transforming monocots are well known to those skilled in the art. Transformation and plant regeneration using these methods have been described for a number of crops including, but not limited to, barley (*Hordeum vulgarae*); maize (*Zea mays*); oats (*Avena sativa*); orchard grass (*Dactylis glomerata*); rice (*Oryza sativa*, including indica and japonica varieties); sorghum (*Sorghum bicolor*); sugar cane (*Saccharum* sp); tall fescue (*Festuca arundinacea*); turfgrass species (e.g. species: *Agrostis stolonifera, Poa pratensis, Stenotaphrum secundatum*); wheat (*Triticum aestivum*), and alfalfa (*Medicago sativa*). It is apparent to those of skill in the art that a number of transformation methodologies can be used and modified for production of stable transgenic plants from any number of target crops of interest.

The transformed plants are analyzed for the presence of the genes of interest and the expression level and/or profile conferred by the promoters of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays.

The seeds of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include seed, endosperm, ovule and pollen. In a particularly preferred embodiment of the present invention, the plant part is a seed.

The following examples are included to demonstrate preferred embodiments of the invention. It should be appreciated that the art is unpredictable, and considerable amount of experimentation may be required even by a person skilled in the art to make and use the claimed inventions. Nonetheless, the kind and amount of experimentation required to make and use the full scope of the subject matter claimed is well within the knowledge and skills of a person with an ordinary level of knowledge and skill in this art to perform without undue experimentation. The techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

This example describes identification and isolation of rice CUT1 (very-long-chain fatty acid condensing enzyme) promoter sequences from rice genomic DNA library.

A publicly known sequence of *Arabadopsis* CUT1 gene (GENBANK ID: AF129511) was used to identify nucleotide sequences generated from rice BAC clones. Comparison of the known CUT1 sequence and BAC sequences was done by using TBLASTN in the BLAST 2.2.1 software suite (Altschul et al., Nucleic Acids Res. 25:3389-3402), with the set of default parameters for pair-wise comparison. Rice BAC libraries were construction, screened and sequenced using commonly known methods, e.g. as disclosed by Tomkins et al. in Plant Mol. Biol., 41:25-32; (1999) and Yu et al. in Theoretical and Applied Genetics, 101: 1093-1099, (2000). An approximately 4-kilo base contiguous nucleotide sequence upstream of the rice CUT1 gene was identified from rice BAC sequences using sequence comparison as described above. Two PCR primers were designed based on the newly identified promoter DNA sequence-in the rice BAC clones. The first primer was designed from within the CUT1 gene extending toward 5' end of the gene DNA sequence of SEQ ID NO: 1. The first primer (referred to as "reverse primer") denoted +60: 3' CACTCTCGTAGCTAGTACG 5' hybridizes approximately 60 base pairs with in the gene extending towards upstream of initiation codon of rice CUT1 gene. The second primer was designed approximately 1769 base pair upstream of rice CUT1 gene's initiation codon extending toward 3' of the gene or the region where reverse primer was designed. The second primer is identified as SEQ ID NO: 2 and is referred as forward primer (−1769F:$^{5'}$ ACTCCCTC-CTCCGTTCTATAAAAA$^{3'}$)

Approximately 100 nanograms of rice genomic DNA with forward and reverse primers was amplified in Master Amp 2X PCR Buffer F (Cat. No. M07205, Epicentre, Madison Wis.) with 20 pico mole of each primer in a total reaction volume of 100 micro liters. PCR amplification was performed in a thermocycler (Model PTC-225, Peltier Thermal Cycle, M J Research, Waltham, Mass.). The thermocycler was programmed to initially heat a reaction mixture of rice genomic DNA, PCR primers, all four nucleotides in buffered solution to 95° C. followed 30 cycles of thermal cycling. Each thermal cycle consisted of 95° C., for 1 minute, 51° C., for 30 seconds and 72° C., for 3 minutes. After amplification the DNA was stored at chilled condition (4° C.). The amplified DNA was cloned by using pGEM®-T Easy Vector System II as per the instructions of manufacturer (Cat. No: A1380, Promega, Madison, Wis.) to identify an authentic clone by sequencing and sequence comparison. A clone with the CUT1 promoter was identified as having an inserted sequence of SEQ ID NO: 3 at it cloning site.

Persons of ordinary skill in the art can use SEQ ID NO:3 to design primers to amplify and clone promoters of this invention.

Example 2

This example describes the construction of a plant transformation vector having a CUT1 promoter to express a marker gene, e.g. beta-glucuronidase from *E. coli* (GUS).

Cloned promoter DNA was re-amplified from the vector produced in Example 1 by using a pair of primers, (5' CAC TAG AGA TCT TCC CTC CTC CGT TC 3' (SEQ ID NO:4) and 5' GGA ATC GCG ATG AAT GAT CGA TGC (SEQ. ID NO: 5) by using PCR reaction, essentially as disclosed in Example 1. The resulting amplicon was re-cloned in a vector by using InsT/Aclone™ PCR Product Cloning Kit as per the instruction of the manufacturer (Catalog No. K1214, FERMENTAS INC, Hanover, Md.). The re-cloned CUT1 promoter was analyzed for its authenticity by restriction analysis and sequencing.

The re-cloned promoter was removed by Bgl II and NruI restriction for cloning in a plant transformation vector. Approximately 1.8 Kilo-bases of promoter fragment was purified by electrophoresis over an agarose gel. Purified promoter DNA with Bgl II and NruI ends was cloned at BamHI and StuI restricted sites to make a plant transformation vector with the elements shown in FIG. 1

Example 3

This example illustrates methods for optimizing CUT1 promoters including the removal of transposable elements.

A transposable element was identified through sequence similarity match to a curated transposable element (TE) sequence database. At the time of the analysis, the ever-growing database consisted of 5,473 TE sequences comprising of approximately 6.4 Mega bases, from public data sources of crops and plant model organisms (available from The Institute for Systems Biology, 1441 North 34th Street, Seattle, Wash.). The sequence match was done using Repeat-Masker™. program developed by Smit, A. F. A, & Green, P, Washington University, Saint Louis Mo. The rice Cutile-1 promoter was initially selected as an 1827 bp sequence upstream of coding region of Cuticle-1 (CUT-1) gene as shown in SEQ ID NO: 3. Through the bio-informatic analysis, we identified a potential transposable element at the 5' end of the sequence. An optimized version of the promoter sequence is provided by removing the potential transposable element from the 5' end from bases 1 to 131, leaving the segment 132 to 1827 bp as an "optimized" promoter, identified as SEQ ID NO: 6.

Example 4

This example illustrates the transformation of a corn plant with DNA constructs for expressing a beta-glucuronidase marker gene by a rice CUT1 promoter.

Transgenic corn was produced by particle bombardment transformation methods as described in U.S. Pat. No. 5,424,412. The plant transformation vector prepared in Example 2, was digested with suitable restriction endonucleases to isolate a plant expression cassette capable of expressing *E. coli* β-glucuronidase in corn plants. The desired expression cassette was purified by agarose gel electrophoresis, and then bombarded into 3-5 days pre-cultured, zygotic immature embryos using a Biolistic® (Dupont, Wilmington, Del.) particle gun with purified isolated DNA fragment as per the instruction of manufacturer. The bombarded immature embryos were selected on selection media supplemented with 500 mg/l of paramomycin (Sigma Chemical Co. Saint Louis Mo., Catalog. No. P8692) to regenerate whole plants (Armstrong, C. L., et al.; Maize Genetics Coop Newsletter; 65: 92-93; 1991). Regenerated plants were grown under greenhouse conditions. Fertile seed was collected, planted and the paramomycin tolerant phenotype was back crossed to produce homozygous seed Example 5

This example illustrates the analysis of CUT1 promoter expression patterns in corn plants. Qualitative and quantitative analysis in desired plant tissue was performed using histochemical and MUG Assay (Jefferson et al. EMBO J.; 6: 3901-3907; 1987).

The MUG assays provide a quantitative analysis of the leaf, embryo, endosperm and other tissue expression in the transgenic plants. Total protein was extracted from desired plant tissue by dissecting different tissue from transgenic corn plants. Plant tissue from un-transformed plant at same growth stage was used as negative control. The MUG assay used 500 microliter of GUS extraction buffer added to the tissues, and tissues were ground with a teflon pestle in 1.5 ml eppendorf tube and centrifuged at 10K RPM for 5 min at 4 degree (Beckman GS-15R). 400 microliter (100 microliter) of supernatant was transferred to a fresh 96-deep well plate. The extracts are frozen on dry ice and stored at −80 till use. The MUG assay consisted of generating a standard curve of activity with a serial dilution of 4-methyl umbelliferone (SIGMA M1381) from 10 picomoles to 800 picomoles. 5 microliter of each extract was added to a flat bottom 96-well plate (Falcon 3872) in duplicate after the plant was preread for blanking the background. 45 microliter of assay solution (0.1 M KPO$_4$ pH7.8, 1.0 mM EDTA, 5% glycerol, 10.0 mM DTT, 2 mM 4-methyl umbelliferyl glucuronide Fluka 69602) was added to each well and mixed with the samples by pipetting. The Plate was incubated at 37° C. for 1 hour, at the end of 1 hour reaction was stopped by adding 350 microliter of 0.2 M Na2CO3 buffer. Fluorescence was measured with excitation at 365 nm, emission at 445 nm using Fluoromax-3 with Micromax Reader (Jobin Yvon Inc., 3880, Park Avenue, Edison, N.J. 08820, USA,), with slit width set at Excitation 2 nm and Emission 3 nm. GUS activity (picomoles/h/microgram protein) was calculated base on MUG results and protein results of each sample. Total protein was assayed using Bio-Rad Protein Assay kit. Serial dilutions of BSA protein from 0.05 mg/ml to 0.5 mg/ml were used for the standard curve. 1.5 microliter of extracts was added to flat bottom 96-well plate (Falcon) in duplicate. 300 ul of diluted dye reagent was added and mixed with the samples. The absorbance at 595 nm was measured KC Junior (Bio-TE, Highland Park, Box:998, Winooski, Vt. 05404-0998, USA) at room temperature after 5 min incubation at room temperature. The MUG analysis demonstrated that the promoter isolated by the afore described invention express in various cell types of corn leaf, root, cob, anther, embryo and endosperm during different developmental stages. Independent transformed corn lines can be selected from the population of plants transformed with the promoters of the present invention that express at different developmental stages of corn leaf, root, cob, anther, embryo and endosperm. Results of quantitative and qualitative expression analysis are show in Table 1 and Table 2 respectively.

Result on table 1 show the quantitative expression pattern caused by the promoter of present invention (Table 1A) in different tissue of corn plant that could be reproduced in a variety of transformed corn events (Table 1B). These results also exhibit that promoter of present invention is capable of causing expression of transgene in a variety of tissue, however levels of expression in different tissue varies. These results clearly suggest that transgene expressed under the control of CUT1 promoter will have great utility to obtain transgenic plants with a variety of genes where differential expression pattern of gene is desired.

On the following Table 1, GUS activity is reported in terms of pico Mole of MU/microgram protein/hour. Enzyme blank was observed to give an activity <0.1 pico Mole of MU/microgram protein/h. Each data point for V3 to V7 stages is an average of at least two plants. Cold treatment of plants was done by exposing plant to 15° Celcius for 24 hours. Plants were desiccated by withholding water till plant moisture content was reduced to 50% as compared to fully hydrated plants. DAG—Days After Germination; DAP—Days After Pollination; VT—Tasseling stage; IS—Imbibed seed; C—coleoptile; R—Root; L—Leaf; V3—three leaf stage; V7—Seven leaf stage; nd—not determined.

TABLE 1 A

| Stages | Organ | Inducer | min. | Range | max. | Mean | ± | SE |
|---|---|---|---|---|---|---|---|---|
| Imbibed seed | Embryo | — | 1.65 | — | 49.88 | 18.86 | ± | 10.68 |
| Imbibed seed | Endosperm | — | 12.23 | — | 12.23 | 12.23 | ± | 0.00 |
| 3 DAG | Root | — | 14.59 | — | 113.81 | 34.51 | ± | 16.06 |
| V3 | Root | — | 11.75 | — | 129.73 | 47.76 | ± | 27.52 |
| V3 | Root | Cold | 11.50 | — | 16.47 | 13.53 | ± | 1.07 |
| V3 | Root | Desiccation | 13.18 | — | 34.05 | 23.61 | ± | 10.43 |
| V7 | Root | — | 58.34 | — | 108.36 | 83.35 | ± | 25.01 |
| VT | Root | — | 0.10 | — | 0.10 | 0.10 | ± | 0.00 |
| 3 DAG | Coleoptile | — | 13.26 | — | 125.32 | 58.14 | ± | 14.83 |
| V3 | Leaf | — | 6.85 | — | 40.57 | 21.90 | ± | 8.30 |
| V3 | Leaf | Cold | 10.30 | — | 30.91 | 20.27 | ± | 5.96 |
| V3 | Leaf | Desiccation | 1.60 | — | 9.37 | 4.51 | ± | 1.05 |
| V7 | Leaf-Mature | — | 4.13 | — | 66.16 | 35.15 | ± | 31.01 |
| V7 | Leaf-Young | — | 0.10 | — | 0.10 | 0.10 | ± | 0.00 |
| VT | Leaf-Mature | — | 0.10 | — | 0.10 | 0.10 | ± | 0.00 |
| VT | Leaf-Senescence | — | 0.10 | — | 0.10 | 0.10 | ± | 0.00 |
| VT | Cob | — | 23.85 | — | 563.77 | 207.82 | ± | 106.21 |
| VT | Anther | — | 5.01 | — | 149.92 | 55.85 | ± | 47.09 |
| 14 DAP | Embryo | — | 21.17 | — | 347.85 | 113.67 | ± | 43.40 |
| 21 DAP | Embryo | — | 20.02 | — | 161.17 | 82.02 | ± | 15.75 |
| 35 DAP | Embryo | — | 30.06 | — | 273.63 | 105.21 | ± | 19.24 |
| 7 DAP | Kernel | — | 10.22 | — | 18.92 | 15.12 | ± | 1.86 |
| 14 DAP | Endosperm | — | 20.28 | — | 255.94 | 75.74 | ± | 14.85 |
| 21 DAP | Endosperm | — | 24.84 | — | 132.19 | 68.67 | ± | 12.75 |
| 35 DAP | Endosperm | — | 37.94 | — | 128.47 | 83.20 | ± | 45.26 |

TABLE 1 B

| Stage | Organ | ZM_B10 546/H99 | ZM_B10 550/H99 | ZM_B10 552/H99 | ZM_B11 434/H99 | ZM_B11 439/H99 | ZM_B11 827/H99 | ZM_B11 833/H99 |
|---|---|---|---|---|---|---|---|---|
| Imbibed seed | Embryo | <0.1 | <0.1 | 1.65 | 11.96 | <0.1 | 49.88 | <0.1 |
|  | Endosperm | <0.1 | <0.1 | <0.1 | <0.1 | 12.23 | <0.1 | <0.1 |
| 3DAG | Root | 9.22 | 13.81 | 7.99 | 6.34 | 8.90 | 31.36 | <0.1 |
|  | Coleoptile | 40.66 | 4.90 | 3.80 | 13.26 | 86.39 | 58.19 | <0.1 |
| V3 | Root (control) | 19.67 | 75.85 | <0.1 | <0.1 | <0.1 | <0.1 | <0.1 |
|  | Leaf (control) | <0.1 | <0.1 | <0.1 | 20.09 | 1.84 | 23.71 | <0.1 |
| V3 | Root (cold) | 4.40 | 9.83 | 12.02 | 13.21 | nd | 5.85 | 1.78 |
|  | Leaf (cold) | 1.16 | 2.94 | 8.28 | 11.95 | nd | 16.30 | <0.1 |

TABLE 1 B-continued

| Stage | Organ | ZM_B10 546/H99 | ZM_B10 550/H99 | ZM_B10 552/H99 | ZM_B11 434/H99 | ZM_B11 439/H99 | ZM_B11 827/H99 | ZM_B11 833/H99 |
|---|---|---|---|---|---|---|---|---|
| V3 | Root (desiccation) | 3.13 | 7.49 | 23.61 | 7.74 | nd | 2.78 | 3.20 |
|  | Leaf (desiccation) | 2.84 | 2.06 | 4.55 | 7.76 | nd | <0.1 | <0.1 |
| V7 | Root | 4.31 | <0.1 | <0.1 | 58.34 | <0.1 | <0.1 | 108.36 |
|  | Leaf-mature | 66.16 | <0.1 | <0.1 | <0.1 | 4.13 | <0.1 | <0.1 |
|  | Leaf-young | <0.1 | <0.1 | <0.1 | <0.1 | <0.1 | <0.1 | <0.1 |
| VT | Root | <0.1 | <0.1 | <0.1 | <0.1 | <0.1 | <0.1 | <0.1 |
|  | Leaf-mature | <0.1 | <0.1 | <0.1 | 14.29 | <0.1 | <0.1 | <0.1 |
|  | Leaf-Senescence | <0.1 | <0.1 | 0.11 | <0.1 | <0.1 | <0.1 | <0.1 |
|  | Internode | nd | nd | nd | nd | nd | nd | nd |
|  | Cob | 6.62 | <0.1 | <0.1 | 542.88 | 52.58 | <0.1 | 28.02 |
|  | Anther | 1.52 | <0.1 | <0.1 | 81.27 | 5.01 | <0.1 | <0.1 |
|  | Pollen | nd | nd | nd | nd | nd | nd | nd |
|  | Silk | nd | nd | nd | nd | nd | nd | nd |
| 7DAP | Kernel | 5.92 | nd | nd | 4.83 | 5.60 | nd | 8.19 |
| 14DAP | Embryo | 48.06 | nd | nd | 142.79 | 14.94 | nd | 67.16 |
|  | Endosperm | 49.54 | nd | nd | 27.77 | 20.49 | nd | 69.61 |
| 21DAP | Embryo | 53.60 | nd | nd | 46.03 | 52.64 | nd | 39.86 |
|  | Endosperm | 5.42 | nd | nd | 33.27 | 59.54 | nd | 57.13 |
| 35DAP | Embryo | 95.72 | nd | nd | 61.51 | 64.99 | nd | 88.99 |
|  | Endosperm | 13.09 | nd | nd | 16.57 | 1.60 | nd | 128.47 |

Result on table 2 show the qualitative expression pattern caused by the promoter of present invention (Table 2) in different cell types of corn plant. These results also exhibit that promoter of the present invention is capable of causing expression of transgene in a variety of cell types of different tissues; however, intensity of blue color in histochemical assay, at different growth stages, varies in different cell types. CUT-1 promoter exhibits expression in stomatal guard cells that could provide unique advantages for making transgenic plants with very special properties. These results clearly suggest that transgene expressed under the control of CUT1 promoter will have great utility to obtain transgenic plants with a variety of genes where differential expression pattern of gene is desired.

On the following Table 2, Cold treatment of plants was done by exposing plant to 15° Celcius for 24 hours. Plants were desiccated by withholding water till plant moisture content was reduced to 50% as compared to fully hydrated plants. DAG—Days After Germination; DAP—Days After Pollination; VT—Tasseling stage; IS—Imbibed seed; C—coleoptile; R—Root; L—Leaf; V3—three leaf stage; V7—Seven leaf stage.

TABLE 2

| Stage | Inducers | Tissue | Cell Types where expression is observed |
|---|---|---|---|
| Imbibed Seed | — | Seed | Scutellum & Embryo |
| 3 DAG | — | Root | Epidermis, Cortex, Endoderm, Stele, Root Hair and Root Tip |
| V3 | — | Root | Stele |
| V3 | Cold | Root | Epidermis |
| V3 | Desiccation | Root | Epidermis |
| V7 | — | Root | Epidermis and Stele |
| VT | — | Root | Epidermis and Endoderm |
| 3 DAG | — | Apical regions | Coleoptiles |
| V3 | — | Leaf | Epidermis, Guard Cells, Bundle Sheath |
| V3 | Cold | Leaf | Epidermis & Vascular Bundle |
| V3 | Desiccation | Leaf | Epidermis, Bundle Sheath & Vascular Bundle |
| V7 | — | Leaf-source | Epidermis, Bundle Sheath & Stomata |
| V7 | — | Leaf-sink | Epidermis, Bundle Sheath & Stomata |
| VT | — | Leaf (source) | Epidermis, Bundle Sheath & Stomata |
| VT | — | Leaf (senescent) | Expression not observed |
| V7 | — | Node | Vascular Bundle |
| VT | — | Node | Vascular Bundle |
| V7 | — | Internode-elongating | Vascular Bundle |
| VT | — | Internode-elongated | Vascular Bundle |
| V7 | — | spikelet | Rachis Primordia |
| VT | — | spikelet | Expression not observed |
| V7 | — | Cob | Cob Primordia |
| VT | — | Cob | Cob Vasculature, Pedicel, Silk, Glume/Palea & Carpel |
| 7 DAP | — | Kernel | Pericarp & Pedicel |
| 14 DAP | — | Kernel | Aleurone & Pedicel |

TABLE 2-continued

| Stage | Inducers | Tissue | Cell Types where expression is observed |
|---|---|---|---|
| 21 DAP | — | Kernel | Aleurone, Pedicel, Embryo, Scutellum |
| 35 DAP | — | Kernel | Pericarp, Pedicel, Embryo & Scutellum |

Example 6

This example illustrates the utility of derivatives of the native rice CUT1 promoter. Derivatives of the CUT1 promoter are generated by introducing mutations into the nucleotide sequence of the native rice promoter as disclosed in U.S. Pat. No. 6,747,189, incorporated herein by reference. A plurality of mutagenized DNA segments derived from the rice CUT1 promoter including derivatives with nucleotides deletions and modifications are generated and inserted into a plant transformation vector operably linked to a GUS marker gene. Each of the plant transformation vectors are prepared essentially as described in Example 2 except that the full length CUT1 promoter is replaced by a mutagenized derivative of the CUT1 promoter. Corn plants are transformed with each of the plant transformation vectors and analyzed for expression of the GUS marker to identify those mutagenized derivatives having promoter activity.

Example 7

This example illustrates the utility of modified promoters derived from the native rice CUT1 promoter. Fragments of the CUT1 promoter are generated by designing primers to clone fragments of the native rice promoter. A plurality of cloned fragments of the CUT1 promoter ranging in size from 50 nucleotide up to about full length are obtained using the methods of Example 1 except that the primers are designed for fragments instead of the full length promoter. 3' fragments from the 3' end of the rice CUT1 promoter comprising the CAAT and TATA boxes and random fragments of about 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600 and 1650 nucleotides in length from various parts of the CUT1 promoter are obtained and inserted into a plant transformation vector operably linked to a GUS marker gene. Each of the plant transformation vectors are prepared essentially as described in Example 2 except that the full length CUT1 promoter is replaced by a fragment of the CUT1 promoter or a combination of a 3' fragment and a random fragment. Corn plants are transformed with each of the plant transformation vectors and analyzed for expression of the GUS marker to identify those fragments having promoter activity.

Example 8

This example illustrates the identification and isolation of CUT1 promoters from organisms other than rice using the native rice CUT1 promoter DNA sequence of SEQ ID NO:6 and fragments to query genomic DNA from other organisms in a publicly available nucleotide data bases including GENBANK. DNA sequences ranging of at least 1000 nucleotides and at least 85% identity to sequence within SEQ ID NO:6 are identified as being part of a putative CUT1 promoter. The full promoters are cloned and inserted into a plant transformation vector which is used to transform corn plants essentially as illustrated in Example 7 to verify promoter activity and CUT1 promoter expression patterns.

We claim:

1. An isolated DNA molecule having promoter function and comprising
   (a) at least 50 contiguous bases from SEQ ID NO:6 comprising rice CUT1 promoter activity;
   (b) a sequence comprising SEQ ID NO:6; or
   (c) a fragment of SEQ ID NO:6 comprising rice CUT1 promoter activity,
   wherein the DNA molecule having promoter function is operably linked to a heterologous transcribable DNA molecule.

2. A recombinant DNA expression cassette having a promoter comprising the DNA molecule of claim 1.

3. A transgenic plant having in its genome a recombinant DNA expression cassette of claim 2.

4. A seed of a transgenic plant of claim 3, wherein the seed comprises the expression cassette of claim 2.

5. The seed of claim 4 wherein said transgenic plant is selected from the group consisting of corn, soybean, cotton wheat, rice and canola, and wherein the seed comprises the expression cassette of claim 2.

6. A cell transformed with the DNA molecule of claim 1.

7. The isolated DNA molecule of claim 1, wherein the DNA molecule comprises SEQ ID NO:6.

8. The transgenic plant of claim 3, wherein the DNA molecule comprises SEQ ID NO:6.

9. The seed of claim 4, wherein the DNA molecule comprises SEQ ID NO:6.

10. The cell of claim 6, wherein the DNA molecule comprises SEQ ID NO:6.

11. The isolated DNA molecule of claim 1, wherein the DNA molecule comprises at least 50 contiguous bases from SEQ ID NO:6 comprising rice CUT1 promoter activity.

12. The isolated DNA molecule of claim 1, wherein the DNA molecule comprises a fragment of SEQ ID NO:6 comprising rice CUT1 promoter activity.

13. The recombinant DNA expression cassette of claim 2, wherein the wherein the DNA molecule comprises SEQ ID NO:6.

14. The recombinant DNA expression cassette of claim 2, wherein the wherein the DNA molecule comprises a fragment of SEQ ID NO:6 comprising rice CUT1 promoter activity.

15. The transgenic plant of claim 3, wherein the DNA molecule comprises at least 50 contiguous bases from SEQ ID NO:6 comprising rice CUT1 promoter activity.

16. The transgenic plant of claim 3, wherein the DNA molecule comprises a fragment of SEQ ID NO:6 comprising rice CUT1 promoter activity.

17. The seed of claim 4, wherein the DNA molecule comprises at least 50 contiguous bases from SEQ ID NO:6 comprising rice CUT1 promoter activity.

18. The seed of claim 4, wherein the DNA molecule comprises a fragment of SEQ ID NO:6 comprising rice CUT1 promoter activity.

19. The cell of claim 6, wherein the DNA molecule comprises at least 50 contiguous bases from SEQ ID NO:6 comprising rice CUT1 promoter activity.

20. The cell of claim 6, wherein the DNA molecule comprises a fragment of SEQ ID NO:6 comprising rice CUT1 promoter activity.

* * * * *

UNITED STATES PATENT AND TRADEMARK OFFICE
CERTIFICATE OF CORRECTION

PATENT NO. : 7,408,055 B2  Page 1 of 1
APPLICATION NO. : 11/352157
DATED : August 5, 2008
INVENTOR(S) : Dasgupta et al.

It is certified that error appears in the above-identified patent and that said Letters Patent is hereby corrected as shown below:

In claim 13, column 20, line 18, delete the duplicate wording of "wherein the"

In claim 14, column 20, line 21, delete the duplicate wording of "wherein the"

Signed and Sealed this

Fourteenth Day of October, 2008

JON W. DUDAS
*Director of the United States Patent and Trademark Office*